(12) United States Patent
Jemelin

(10) Patent No.: US 8,637,128 B2
(45) Date of Patent: Jan. 28, 2014

(54) CYCLIC OLEFIN COPOLYMER EXTERNAL CAPSULE FOR PRESERVING MEDICAL DEVICE

(75) Inventor: Vincent Jemelin, Magden AG (CH)

(73) Assignee: Straumann Holding AG, Basel (CH)

( * ) Notice: Subject to any disclaimer, the term of this patent is extended or adjusted under 35 U.S.C. 154(b) by 422 days.

(21) Appl. No.: 10/575,981

(22) PCT Filed: Oct. 15, 2004

(86) PCT No.: PCT/EP2004/011673
§ 371 (c)(1),
(2), (4) Date: Apr. 17, 2006

(87) PCT Pub. No.: WO2005/039435
PCT Pub. Date: May 6, 2005

(65) Prior Publication Data
US 2007/0068827 A1    Mar. 29, 2007

(30) Foreign Application Priority Data

Oct. 16, 2003  (EP) ..................................... 03023619

(51) Int. Cl.
*B32B 1/02*    (2006.01)
*A61B 19/02*   (2006.01)
(52) U.S. Cl.
USPC ....... 428/35.7; 428/35.2; 428/35.3; 428/35.5; 428/35.8; 428/36.6; 428/36.92; 206/63.5
(58) Field of Classification Search
USPC ........... 428/34.1, 34.4, 34.6, 34.7, 35.2, 35.3, 428/35.5, 35.7, 35.8, 36.6, 36.92; 206/63.5
See application file for complete search history.

(56) References Cited

U.S. PATENT DOCUMENTS

| 3,757,979 | A | * | 9/1973 | Berghahn | 215/225 |
| 5,723,189 | A | * | 3/1998 | Sudo | 428/36.9 |
| 5,853,833 | A | * | 12/1998 | Sudo et al. | 428/36.6 |
| 6,261,097 | B1 | | 7/2001 | Schmutz et al. | |
| 6,431,350 | B1 | * | 8/2002 | Pieroni et al. | 206/63.5 |
| 6,793,101 | B2 | * | 9/2004 | Shinozaki et al. | 222/153.02 |
| 2004/0067467 | A1 | * | 4/2004 | Gault | 433/173 |
| 2005/0106534 | A1 | * | 5/2005 | Gahlert | 433/173 |
| 2006/0046229 | A1 | * | 3/2006 | Teich | 433/173 |

FOREIGN PATENT DOCUMENTS

| JP | 10-129642 | 5/1998 |
| JP | 10-181735 | 7/1998 |
| JP | 11-005721 | 1/1999 |
| JP | 2002-205725 | 7/2002 |
| JP | 2004-018579 | 1/2004 |
| WO | WO 02/38452 A1 | 5/2002 |
| WO | WO 03/024511 A1 | 3/2003 |

OTHER PUBLICATIONS

JP 10-181735 machine translation, Kishimoto et al., Oct. 31, 1998.*

* cited by examiner

*Primary Examiner* — Walter B Aughenbaugh
(74) *Attorney, Agent, or Firm* — Scully, Scott, Murphy & Presser, P.C.

(57) ABSTRACT

A package for holding fluid material suitable for preserving a dental implant is disclosed. The package has a capsule and a cap. The capsule is formed exclusively of cyclic olefin copolymer with an impermeability to moisture of less than 5% fluid loss per year and the cap is formed of low density polyethylene.

10 Claims, 2 Drawing Sheets

CYCLIC OLEFIN COPOLYMER EXTERNAL CAPSULE FOR PRESERVING MEDICAL DEVICE

The present invention provides for an external capsule for holding fluid material suitable for preserving a medical device or the like, wherein the external capsule has a main body formed of cyclic olefin copolymer (COC). Furthermore, the present invention also provides for a package with an external capsule for preserving a dental implant or the like of the type described in U.S. Pat. No. 6,261,097 which was assigned to the assignee of the present invention and the full content of which is herewith incorporated by reference.

BACKGROUND OF THE INVENTION

Medical devices such as dental implants may require for a better and long-term preservation to be stored in a fluid.

To ensure a proper functioning of medical devices, they need to be protected from undergoing changes during the storage.

The primary package with the external capsule wherein the medical devices are stored should then contain a fluid, whose composition, characteristics and quantity should be kept constant for a long period of time.

Also the environmental condition (e.g. high humidity or dryness) should not alter the properties of the stored fluid and thus of the device immersed in said fluid, so as to ensure the same preservation standard all over the world.

SUMMARY OF THE INVENTION

It is therefore an object of the present invention to provide for an external capsule for holding fluid material suitable for preserving a medical device such as a dental implant, wherein the external capsule is formed of a material which ensures a good long time storage and which is not influenced by environmental condition.

Another object of the present invention is to provide for a package with an external capsule for preserving a dental implant in a fluid, such that to ensure a good, long time storage and avoid influence by environmental condition.

The above object as well as further objects which will become apparent hereinafter are achieved by an external capsule as defined in independent claim 1 and by a package for preserving a medical device or the like as defined in independent claims 2 through 4. Further advantageous aspects of the invention are set forth in the dependent claims.

BRIEF DESCRIPTION OF THE DRAWINGS

The foregoing and other objects, features, and advantages of the invention, as well as presently preferred embodiments thereof, will become more apparent from a reading of the following description, in connection with the accompanying drawings in which.

DESCRIPTION OF THE PREFERRED EMBODIMENTS

Figure 1:
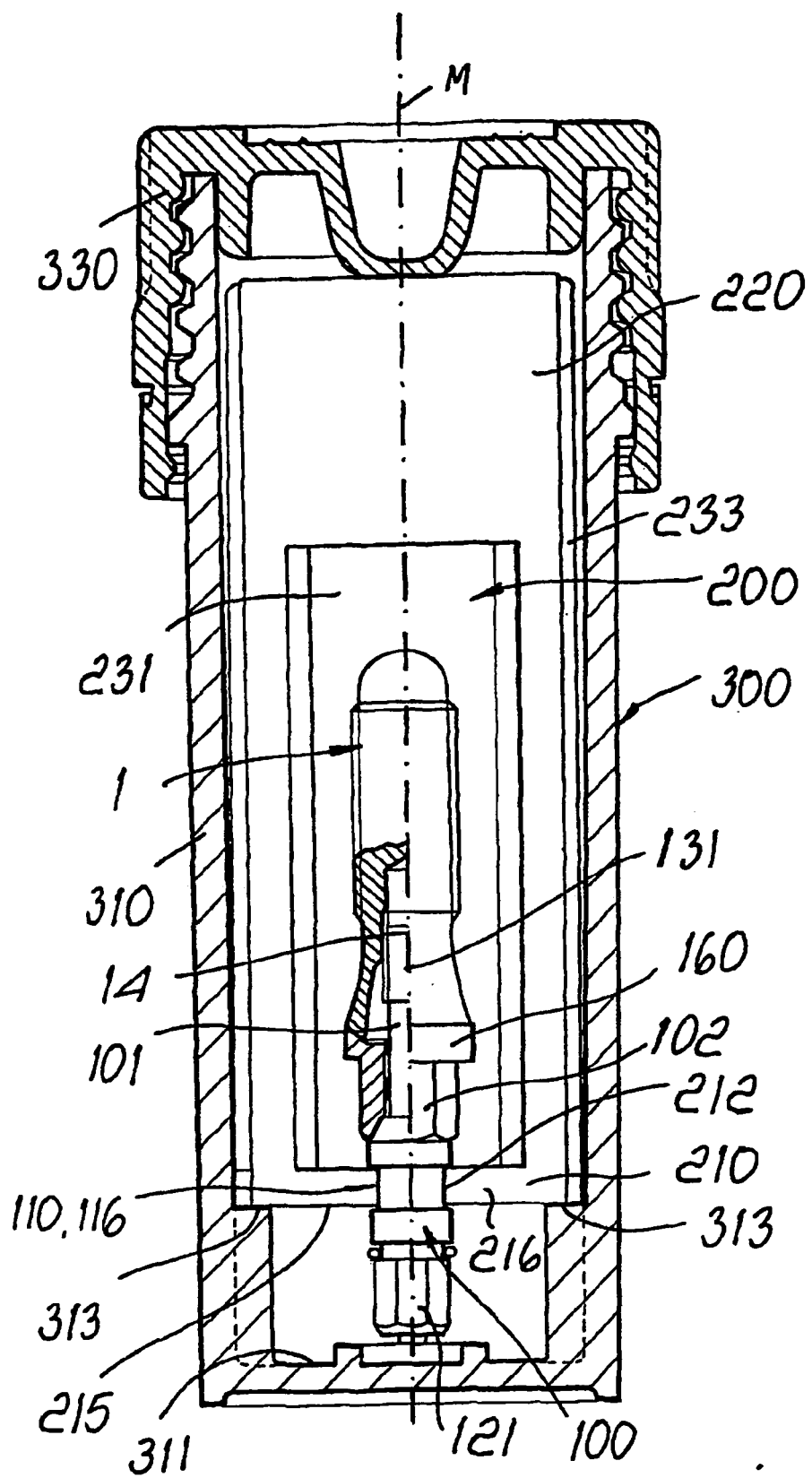
FIG. 1 is a generic package with an external capsule as shown in the prior art according to U.S. Pat. No. 6,261,097.

With reference to FIG. 1 there is shown a generic package with an external capsule and an ampule for a dental implant as known from U.S. Pat. No. 6,261,097.

According to U.S. Pat. No. 6,261,097 there is provided, as shown in prior art FIG. 1, an implant 1 and a holding element 100 with an extension element 121 releasably associated with the implant 1. In the assembled state, an ampoule 200, with the implant 1 held therein by the holding element 100, is inserted into an external capsule 300. The external capsule 300 comprises a hollow cylinder 310, the base 311 of which is closed, and a screw-on closure cap 320. On the inside of the cylinder 310, parallel to and at a distance from the base 311, there is a support shoulder 313, which is intended to act as an axial stop for the first planar base side on a fixing part 210 of the inserted ampoule 200. In this case, the support shoulder 313 comprises four webs which are offset through 90 DEG in each case. The closure cap 320 points towards a stand part 220 of the ampoule 200. At most in the region of the clearance between the second planar base side on the stand part 220 and the closure cap 320, the ampoule 200 can move on the axis M and otherwise lies in a stable position in the external capsule 300 in the event of vibrations.

The implant 1 is held by a holding element 100 with a screw 101 and a sleeve part 102. An externally threaded part 131 of the screw 101, which projects through the sleeve part 102, engages in an internally threaded bore 14 on the implant 1, while a mating shoulder 161 of a shoulder part 160 of the sleeve part 102 rests on an implant shoulder. A fixing part 110 of the holding element 100 is latched into the fixing part 210 of an ampoule 200, i.e. the cylindrical section 116 of the holding element 100 is clamped in a laterally open indent 212 in the ampoule 200 and is surrounded laterally by the two jaws 215, 216. The annular shoulders of the holding element 100 bear against the fixing part 210 on both sides. In this way, the implant 1 is held in line with the center axis M inside the ampoule 200 without coming into contact with the ampoule 200.

The Applicants of the present invention found that the control of the above mentioned parameters, namely the composition characteristics and quantity of the fluid may be achieved by an appropriate external capsule. In addition, the control can be improved by an appropriate overall package. Particularly relevant for this purpose is the selection of the material from which the external capsule and/or the package are made. In fact, in a device manufactured according to the principles of the present invention the liquid level could be kept constant over a period of 5 years.

Specifically it has-been found that in order to prevent evaporation of the fluid present in the external capsule or in the overall package, the material that constitutes said external capsule and/or the overall package should posses a low water or fluid vapor permeability and a low gas permeability.

Glass generally offers an excellent low water vapor and low gas permeability. Furthermore, it is transparent, and thus allows the device to be seen by the user, this being an highly desirable characteristic. However, glass containers are not easy to be handled in that they are heavy and breakable.

The conventional polymers used in the medical package field such as styrene butadiene copolymer (SBS), Poly(m-ethyl methacrylate) (PMMA), polystyrene (PS) and polyester (PET) do not offer the desired low water vapor and gas permeability that allows a long term storage of the medical device.

In view of the above there is then the need of new containers for medical devices to be stored in a fluid which offer the advantage of the glass container (low water vapor, low gas permeability, and transparency) without however being affected by the drawbacks of the containers made of glass. Moreover, there is the need to avoid the disadvantages of the conventional polymers.

Figure 2:
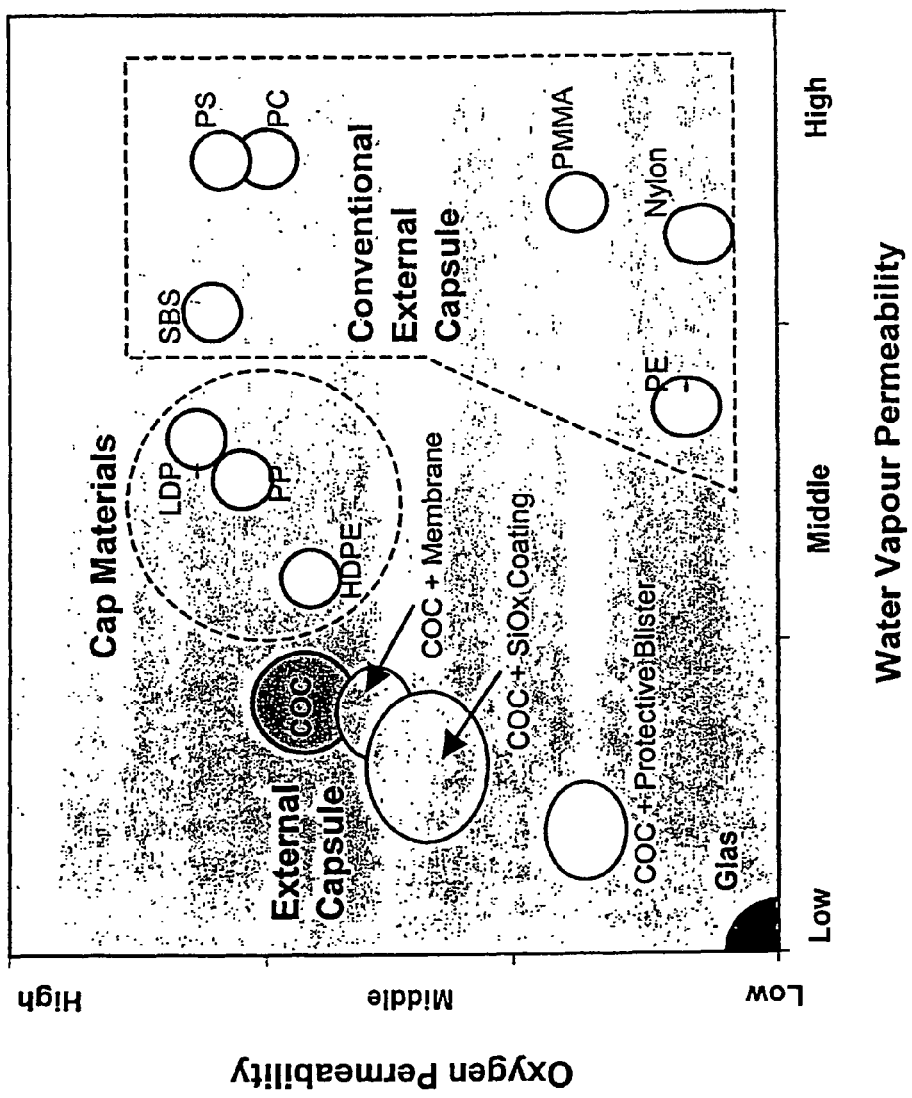
FIG. 2 is a plot which shows a relative comparison of the oxygen and water vapor permeability of various components of a package including an external capsule, a cap etc. formed with various materials.

Accordingly, the Applicants have found that the external capsule is advantageously manufactured from cyclo-olefin copolymer (COC) or the like, which is a plastic material with an excellent impermeability to moisture (less than 5%, preferably less than 1% fluid loss per year) and good impermeability to gas, as shown in FIG. 2. At the same time COC is transparent and can be sterilized and has full medical device certification (FDA, CE). COC may also advantageously be used to manufacture the ampoule in view of its good hydrophobic properties (less than 0.01% fluid absorption in 24 hours at 23° C.), such that the overall shape of the ampoule does not change while immersed in a fluid.

COC also combines excellent electrical properties with low density, high stiffness and strength therefore leading to a light, resistant overall package. Because of the chemical structure of the COC it emits no ions or heavy metals that could affect the stored fluid.

Moreover, an improvement in the oxygen and fluid vapor impermeability can be achieved by coating the COC of the external capsule with a SiOx coat, as shown in FIG. 2.

The cap of the present package may be advantageously manufactured from a polymer. High density polyethylene (HDPE) or low density polyethylene (LDPE) has proven to be particularly advantageous for caps. Also polypropylene (PP) was proven to perform in a satisfactory manner for certain application.

Further, the cap can be replaced by a sealing barrier or used together with the sealing barrier, such that a particularly good impermeability is provided in conjunction with the external capsule made of COC. Preferably, the sealing barrier is embodied as an aluminum membrane closing the open end of the capsule. Nevertheless, titanium or polymer membranes can also be used.

In addition, the combination of a COC capsule with a HDPE or LDPE cap and/or the sealing barrier provides for an excellent shelf life of the medical device stored therein, particularly if a storage fluid, such as an electrolyte or an aqueous solution, is used. The shelf life is further improved by the COC ampoule which does not change its shape by soaking up with fluid.

The overall package impermeability can be improved by including the package in a protective blister (FIG. 2).

The foregoing description of the invention, including the preferred embodiments thereof, has been presented for the purpose of illustration and description. It is not intended to be exhaustive nor is it intended to limit the invention to the precise form disclosed. It will be apparent to those skilled in the art that the disclosed embodiments may be modified in light of the above teachings. In particular, a person skilled in the relevant art will readily understand that the external capsule/package and the ampoule are not limited to the use with dental implants. Rather the external capsule/package and the ampoule may by used in connection with other medical or non-medical devices providing the same handling and sterility maintenance advantages as described hereinbefore. Furthermore, the present invention is not limited to the package shown in present prior art FIG. 1 according to U.S. Pat. No. 6,261,097 but may be used with any kind of similar packages, such as those according to the concurrently filed application with the title "Package for Preserving a Medical Device or the Like", the full content of which is also herewith incorporated by reference.

The embodiments described are chosen to provide an illustration of principles of the invention and its practical application to enable thereby one of ordinary skill in the art to utilize the invention in various embodiments and with various modifications as are suited to the particular use contemplated. Therefore, the foregoing description is to be considered exemplary, rather than limiting, and the true scope of the invention is that described in the following claims.

Where technical features mentioned in any claim are followed by reference signs, those reference signs have been included just for the sole purpose of increasing intelligibility of the claims and accordingly, such reference signs do not have any limiting effect on the scope of each element identified by way of example by such reference signs.

The invention claimed is:

1. A package for holding a dental implant and for containing a fluid material suitable for preserving the dental implant, the package including a capsule and a cap, wherein the capsule consists of cyclic olefin copolymer with an impermeability to moisture of less than 5% fluid loss per year and wherein the cap is formed of low-density-polyethylene, wherein the package further includes an ampoule within the capsule, the ampoule being also formed of cyclic olefin copolymer.

2. The package of claim 1, further including a barrier sealing the capsule, wherein the barrier is preferably formed of aluminum.

3. The package of claim 1, wherein the package is contained in a protective blister.

4. A combination comprising:
a dental implant,
a fluid material suitable for preserving the dental implant, and
a package configured to hold the dental implant therein and to contain the fluid material therein, the package comprising a capsule and a cap, wherein the capsule consists of cyclic olefin copolymer with an impermeability to moisture of less than 5% fluid loss per year and wherein the cap is formed of low-density-polyethylene.

5. The combination of claim 4, wherein the package further comprises an ampoule within the capsule, the ampoule being also formed of cyclic olefin copolymer.

6. The combination of claim 4, wherein the cap comprises first threads and the capsule comprises second threads, the first threads and the second threads engaging each other to close the capsule.

7. The combination of claim 4, wherein the package is contained in a protective blister.

8. A package for holding a dental implant and for containing a fluid material suitable for preserving the dental implant, the package including a capsule and a cap, wherein the capsule consists of cyclic olefin copolymer with an impermeability to moisture of less than 5% fluid loss per year and wherein the cap is formed of low-density-polyethylene, wherein the package is contained in a protective blister.

9. The package of claim 8, further comprising a barrier sealing the capsule, wherein the barrier is preferably formed of aluminum.

10. The package of claim 8, further comprising an ampoule within the capsule, the ampoule being also formed of cyclic olefin copolymer.

* * * * *